(12) United States Patent
Bondhus et al.

(10) Patent No.: US 9,295,829 B2
(45) Date of Patent: *Mar. 29, 2016

(54) MEDICAL LEADS HAVING FORCED STRAIN RELIEF LOOPS

(71) Applicant: MEDTRONIC, INC., Minneapolis, MN (US)

(72) Inventors: Spencer M. Bondhus, Columbia Heights, MN (US); Bryan D. Stem, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,725

(22) Filed: Sep. 29, 2014

(65) Prior Publication Data

US 2015/0018920 A1      Jan. 15, 2015

Related U.S. Application Data

(63) Continuation of application No. 13/752,548, filed on Jan. 29, 2013, now Pat. No. 8,849,421.

(60) Provisional application No. 61/635,789, filed on Apr. 19, 2012.

(51) Int. Cl.
  *A61N 1/00*   (2006.01)
  *A61N 1/05*   (2006.01)
  *H01R 13/58*  (2006.01)
  *A61N 1/08*   (2006.01)

(52) U.S. Cl.
  CPC .. *A61N 1/05* (2013.01); *A61N 1/08* (2013.01); *H01R 13/5833* (2013.01); *A61N 2001/086* (2013.01); *Y10T 29/4922* (2015.01); *Y10T 29/49208* (2015.01)

(58) Field of Classification Search
  CPC ..... A61N 1/05; A61N 1/08; A61N 2001/086; H01R 13/5833; Y10T 29/49208; Y10T 29/4922
  See application file for complete search history.

(56) References Cited

U.S. PATENT DOCUMENTS

2008/0103545 A1*   5/2008   Bolea et al. ............. 607/42

* cited by examiner

*Primary Examiner* — George Manuel
(74) *Attorney, Agent, or Firm* — Withers & Keys, LLC

(57) ABSTRACT

Strain relief loops are forced by being formed into medical leads such that a body of the lead imposes a force to regain the loop if the loop has been disturbed. Because the strain relief loop is forced, the surgeon implanting the medical lead is not required to create the strain relief loop as a step in the implantation procedure. Forcing the strain relief loop ensures that the strain relief is achieved. The forced strain relief loop also ensures that the loop is present to reduce heating at the electrodes of the medical caused by exposure to excessive radiofrequency energy. The forced strain relief loop may be created by heating the lead body while held in the loop configuration by a mold to cause the loop configuration to persist once the medical lead is removed from the mold.

15 Claims, 5 Drawing Sheets

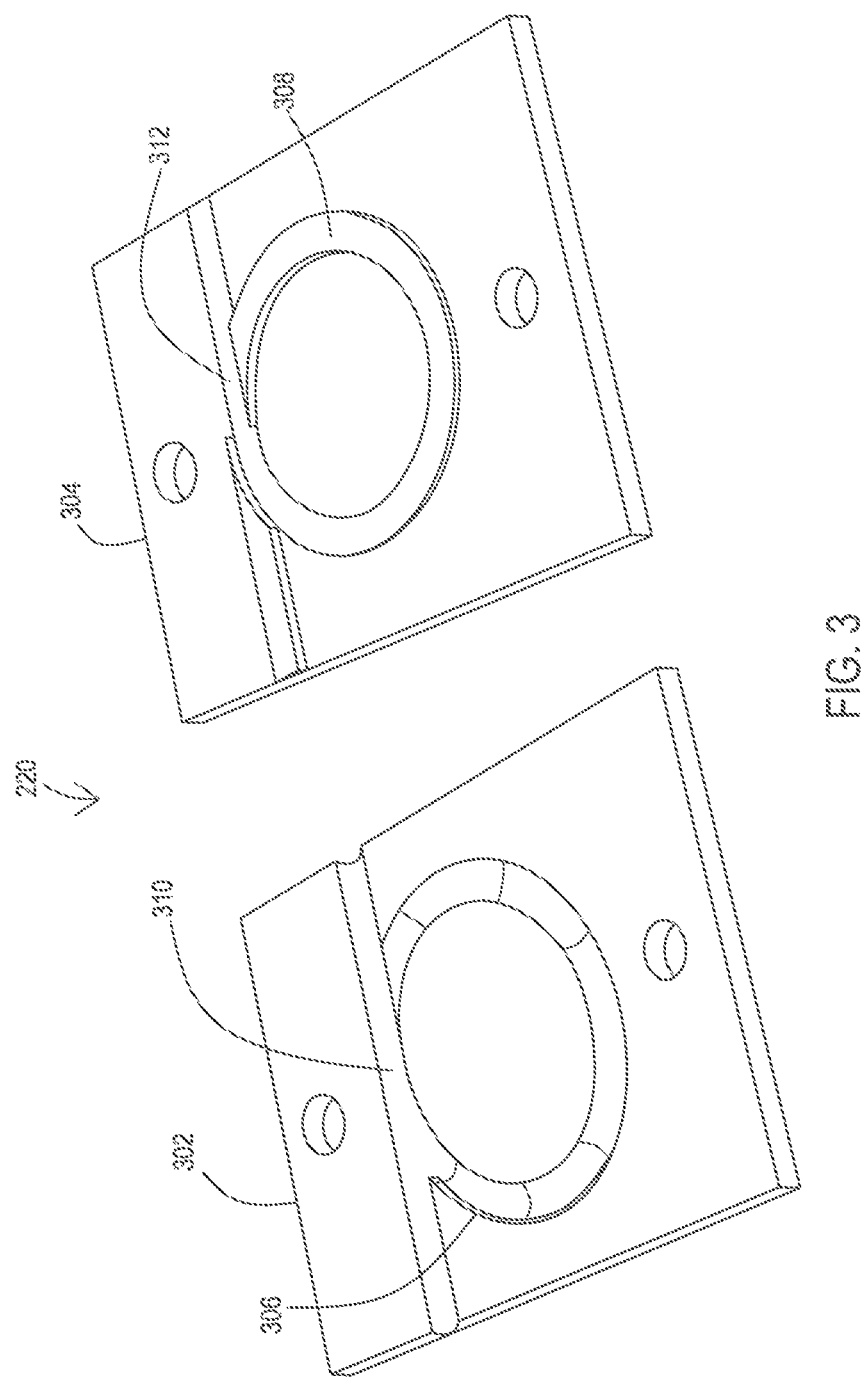

MEDICAL LEADS HAVING FORCED STRAIN RELIEF LOOPS

TECHNICAL FIELD

Embodiments are related to medical leads that carry electrical signals from a medical device. More particularly, embodiments are related to medical leads with forced strain relief loops.

BACKGROUND

Medical leads provide electrical stimulation from a medical device to a target site within a body of a patient. The medical device is typically implanted or otherwise installed on the body in an accessible area at some distance from the target site, and the medical lead is routed to the target site either through a percutaneous procedure or by surgical implantation depending upon the type and size of the medical lead being implanted.

Because the medical lead extends some distance between the medical device and the target site within the body, the medical lead is subject to forces imposed by movements of the patient. In particular, the medical lead may be subjected to strain. To address the strain, the medical lead may be routed by creating a loop that relieves the strain by the loop making available an additional length of the lead.

An additional benefit of the strain relief loop occurs in relation to radiofrequency (RF) heating at the electrodes. RF heating can occur when the patient is exposed to relatively high levels of RF energy such as during a magnetic resonance imaging (MRI) scan. The metal conductors within the lead such as filars connected to the electrodes have current induced by the RF energy. This induced current can produce heating within the medical lead and at the electrodes. The presence of the strain relief loop, particularly if the loop is created in relatively close proximity to the distal end of the medical lead where the electrodes are located, reduces such heating which improves the comfort of the patient and lessens the risk of injury during MRI scans.

An issue is that strain relief loops may be considered optional and/or may be overlooked by some clinicians and therefore are not necessarily created in all instances. Thus, one implantation of a given medical system that includes a strain relief loop may offer better protection for the patient from RF heating than a same medical system that is implanted in a patient without a strain relief loop.

SUMMARY

Embodiments address issues such as these and others by providing medical leads and related systems where the medical lead has a forced strain relief loop. The strain relief loop is forced by having the strain relief loop be formed by a lead body of the medical lead in such a way that the lead body applies force to regain the formed loop whenever the formed loop is disturbed. In this manner, forming the strain relief loop is not a step of the implantation process and therefore is not optional considering the medical lead already has the forced strain relief loop at the time of implantation.

Embodiments provide a medical lead that includes an insulative lead body having a formed loop such that the insulative lead body imposes a force to regain the formed loop when the formed loop is disturbed. The medical lead further includes at least one electrical conductor surrounded by the insulative lead body and at least one electrical contact on a proximal end of the lead body, the at least one electrical contact being electrically coupled to the at least one electrical conductor. The medical lead further includes at least one electrode on a distal end of the lead body, the at least one electrode being electrically coupled to the at least one electrical conductor.

Embodiments provide a medical system that includes a medical device with a stimulation output connector and a medical lead. The medical lead includes an insulative lead body having a formed loop such that the insulative lead body imposes a force to regain the formed loop when the formed loop is disturbed. The medical lead further includes at least one electrical conductor surrounded by the insulative lead body and at least one electrical contact on a proximal end of the lead body, the at least one electrical contact being electrically coupled to the at least one electrical conductor and in electrical contact with the stimulation output connector. The medical lead additionally includes at least one electrode on a distal end of the lead body, the at least one electrode being electrically coupled to the at least one electrical conductor.

Embodiments provide a method of making a medical lead that involves surrounding a conductor with an insulative lead body and mounting a contact on a proximal end of the insulative lead body and in electrical connection to the conductor. The method further involves mounting an electrode on a distal end of the insulative lead body and in electrical connection to the conductor. Additionally, the method involves forming a loop in the insulative lead body such that the insulative lead body imposes a force to regain the formed loop when the formed loop is disturbed.

DESCRIPTION OF THE DRAWINGS

FIG. 3 shows two mold halves that form the strain relief loop onto the medical lead.

DETAILED DESCRIPTION

Embodiments provide forced strain relief loops on medical leads. The strain relief loop is formed on the lead body so that the loop is regained whenever disturbed by force imposed by the lead body. Thus, the strain relief loop is not optional but is present on the medical lead when being implanted and is re-established automatically by the action of the lead body if the loop is manipulated.

Figure 1:
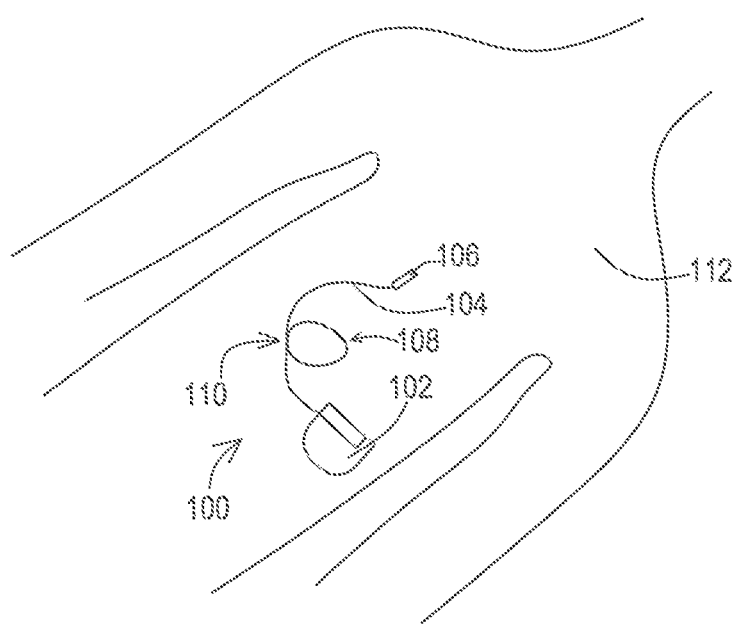
FIG. 1 shows an example of a medical system environment where a forced strain relief loop is present on a medical lead.

FIG. 1 shows an example of a medical system 100 that includes a medical device 102 and a medical lead 104. The medical device 100 produces stimulation signals and the medical lead 104 which is attached to a stimulator output of the medical device 100 delivers the stimulation signals to a set of electrodes 106 on a distal end of the medical lead 104. The set of electrodes 106, such as a paddle having a grid of electrodes, are positioned at a target stimulation site so that the stimulation signals provide stimulation therapy to the body 112 of the patient.

The medical lead 104 includes a forced strain relief loop 108. This strain relief loop 108 is already formed on the lead 104 prior to implantation. Thus, a surgeon implanting the medical lead 104 is not required to form the strain relief loop 108 but instead positions the medical lead 104 including the forced loop 108 within the body of the patient 112. The strain relief loop 108 retains the loop shape during implantation and thereafter. Thus, benefits of the strain relief loop 108 are ensured, such as the strain relief itself as well as the reduction in RF heating should the patient 112 be exposed to significant RF energy such as during an MRI scan.

It has been found that at typical MRI frequencies, producing the medical lead 104 with the forced strain relief loop 108 at between 5 and 15 centimeters from the distal end 106 provides the best level of heating reduction at the distal end 106 where the electrodes are present. The distance of the forced strain relief loop 108 to the distal end may be measured from an intersection point 110 where the medical lead 104 has looped back onto itself which is also referred to as the crossover.

This intersection point 110 tends to develop more heating from RF energy than at other points along the medical lead 104. Therefore, the medical lead 104 may include features to alleviate any issues that might arise from the additional heating at the intersection point 110. These features may be of various forms. Some examples include an increased thickness of the lead body at the intersection point 110 and/or a protective sleeve that covers the intersection point 110. Such examples are discussed in more detail below with reference to FIGS. 4 and 5.

While FIG. 1 shows a single medical lead 104, some embodiments may provide for multiple adjacent medical leads, with each having a loop 108 and the loops may be made adjacent. For example, a distal end 106 with a paddle may have many electrodes such that a single paddle is connected to two adjacent lead bodies. As another example where there are multiple medical leads 104, each lead 104 may have a separate distal end 106 and the forced loops 108 of each lead are may be formed adjacently to one another.

Figure 2:
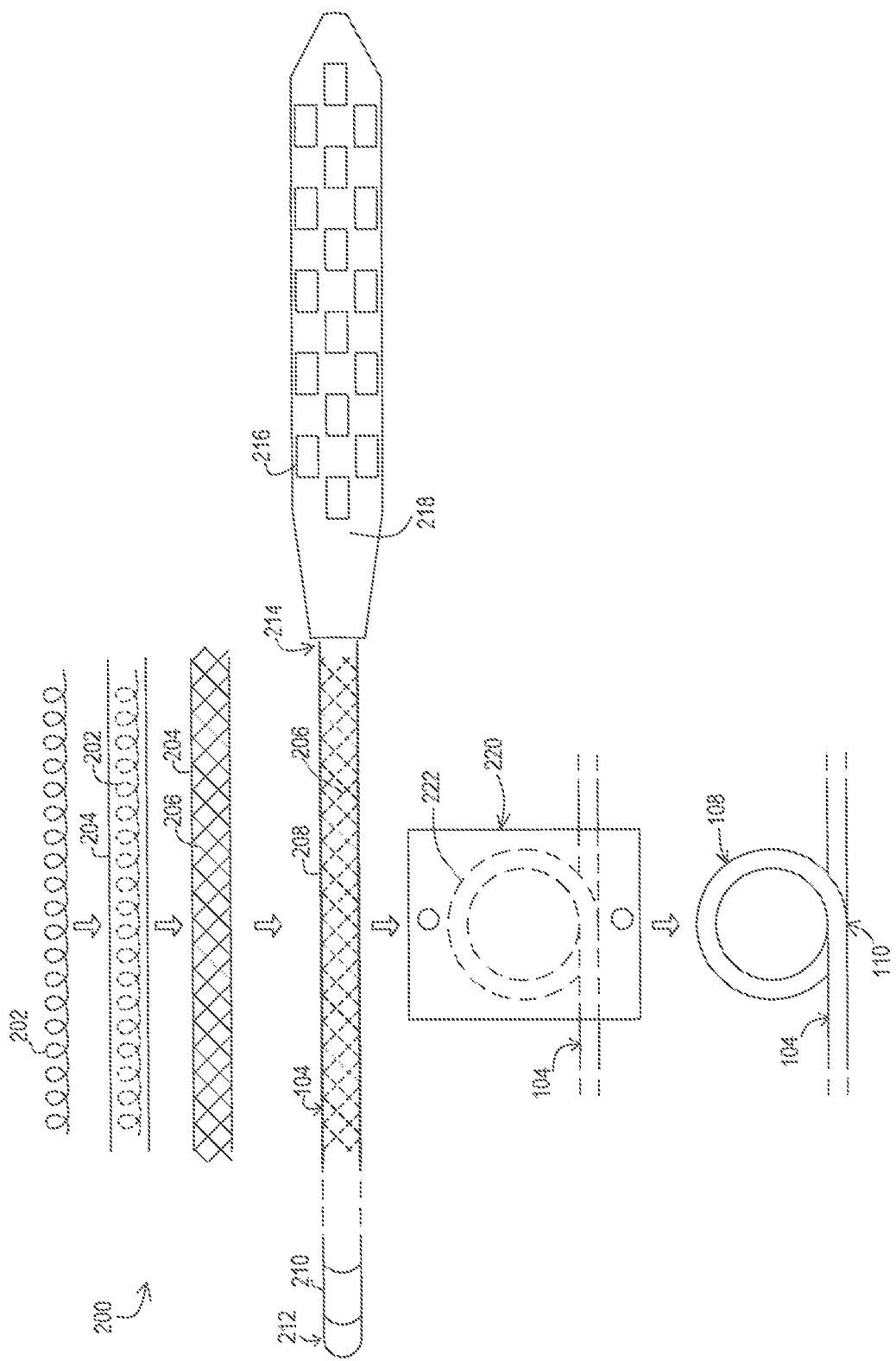
FIG. 2 shows a process for creating an example of a medical lead having a forced strain relief loop.

FIG. 2 shows a process for creating one example of a medical lead 104 with a forced strain relief loop 108. In this example, the process begins with one or more filar conductors 202 which may be coiled filars as shown or may be cabled filars. Generally, there is a filar conductor present for each proximal contact and each distal electrode that will be present on the completed medical lead 104. The one or more conductors 202 may be constructed of various conductive biocompatible materials such as MP35N, MP35N with a silver core, titanium molybdenum, and the like. Each conductor typically has an insulative coating.

In this particular example, an inner insulative lead body layer 204 is fitted to or otherwise applied to surround the one or more conductors 202. The inner insulative lead body layer 204 may surround the conductor either by forming a lumen that the conductor 202 is present within or by encapsulating the conductor 202. The inner insulative lead body layer 204 may be constructed of various non-conductive biocompatible materials such as polyurethane, silicone, silicone-polyetherurethane, and the like. The inner insulative lead body layer 204 may be fitted to the conductors 202 by building the layer 204 separately and then stringing the conductors 202 through the lumen of the layer 204. Alternative manners of applying the layer 204 are also applicable, such as for example extruding or injection molding the layer 204 onto the conductors 202.

In some embodiments, the medical lead 104 may now be ready to have proximal contacts 210 and distal electrodes 216 on a distal paddle 218 installed and also have the forced strain relief loop 108 formed in the lead body layer 204. However, in some cases it may be desirable to provide additional structure such as shielding to further protect the medical lead 104 from unwanted RF heating on the filar conductors 202 and electrodes 216.

In one embodiment for providing such additional structure, a next action taken is to provide a conductive shield 206 about the inner insulative lead body 204. In the particular example shown, the conductive shield 206 is a braided shield that has been placed about the inner insulative lead body 204. The braided shield 206 may be applied in various ways, such as by being braided directly onto the insulative inner lead body 204. The braided shield may be constructed from various biocompatible conductive materials such as tantalum, titanium, and other similarly conductive materials.

The conductive shield 206 may take other forms as well. One example is a foil tube that wraps about the inner insulative lead body 204. Another example is a metallic layer that has been sputtered onto the outer surface of the insulative inner lead body 204. Utilizing a carbon nanotube structure as a dopant or a coating to the body 204 is yet another example.

The shield 206 may then be protected by applying an insulative outer leady body 208 that surrounds the shield 206 and hence the insulative inner lead body 204 and conductors 202. The insulative outer lead body 208 may be constructed of various non-conductive biocompatible materials such as the same materials listed above for the inner body layer 204. The insulative outer lead body layer 208 may be applied in various ways, such as by fitting the layer 208 onto the shield 206 and layer 204 and utilizing a reflow process, extrusion, or injection molding.

In addition to applying the insulative outer lead body 208, the proximal contacts 210 and distal paddle 218 and/or distal electrodes 216 are installed and electrically connected to the corresponding electrical conductors 202 in the conventional manner. At this point, the medical lead 104 is complete. However, the strain relief loop 108 may then be formed in the insulative lead bodies 204 and/or 208 in such a manner to force the strain relief loop 108 to persist on the medical lead 104.

One manner of forming the stain relief loop 108 is to utilize a mold 220 that includes a looped passageway 222 that the medical lead 104 is positioned within at the appropriate point along the medical lead 104. Heat is then applied to the mold 220 and medical lead 104 within the mold 220 to force the strain relief curve to persist in the insulative lead body of the medical lead 104. The medical lead 104 is then removed from the mold 220 and is ready to be packaged for shipment with the forced strain relief loop 108 present. For embodiments where multiple lead bodies are looped adjacently, each lead body may be baked in separate molds and then made adjacent once removed or alternatively, the mold 220 may be sized to accommodate multiple adjacent lead bodies and form the loop 108 in the multiple leads 104 simultaneously.

Some specific examples for heating the medical lead 104 to create the strain relief loop are as follows. In one example, a polyurethane lead body with a hardness of 80 Shore A, the lead 104 is heated at approximately 220 to 270 degrees Fahrenheit for approximately 20-30 minutes. In another example, a polyurethane lead body with a hardness of 55 Shore D, the lead 104 is heated at approximately 230 to 280 degrees Fahrenheit for approximately 20-30 minutes.

An example of the mold 220 is shown further in FIG. 3 in the opened state. Here, the mold 220 has two halves 302, 304. Each half 302, 304 may be constructed of a material such as stainless steel, aluminum, and the like that is capable of holding the lead 104 in the looped configuration while also distributing heat to the medical lead 104. The half 302 includes a looped channel 306 where one direction of the loop has a deeper channel portion 310 at the intersection point to allow the medical lead 104 to cross over itself within the mold 220. Similarly, the half 304 includes a looped channel 308 where one direction of the loop has a deeper channel portion 312 at the intersection point to also allow the medical lead 104 to cross over itself within the mold 220. These two halves 302, 304 are brought into engagement with the medical lead 104 present within the channels 306, 308, and then heat is applied such as by placing the mold 220 including the medical lead 104 within an oven.

Other manners of forcing the strain relief loop 108 are also available. These include bonding the two portions of the outer body 208 together at the intersection point. This bond may be produced in various ways, such as by using an adhesive or by melting the two portions together. The bond may later be broken while preserving the loop upon implanting the lead to maintain the strain relief function of the loop.

Figure 4A:
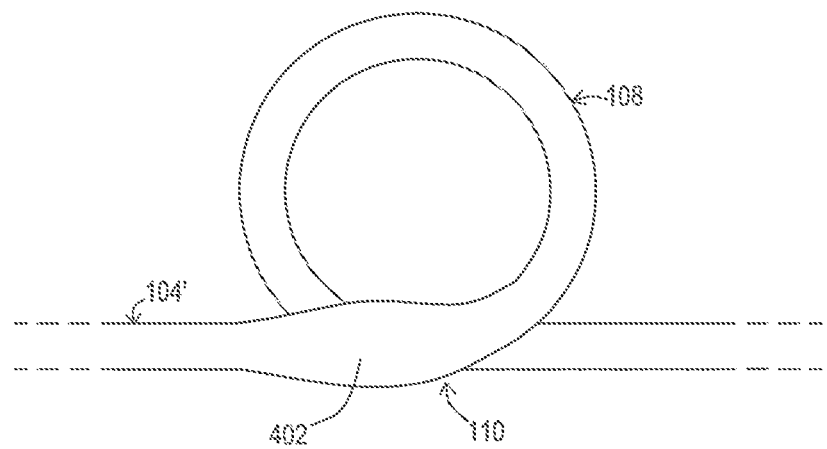
FIG. 4A shows a first view of an example of the forced strain relief loop according to various embodiments of a medical lead.
Figure 4B:
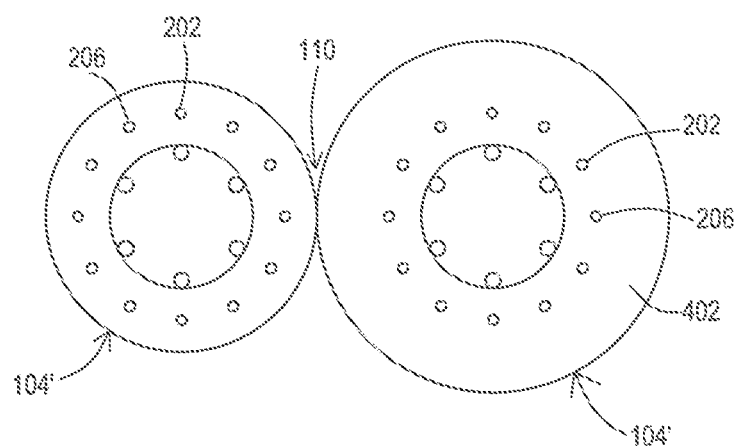
FIG. 4B shows a second view of an example of the forced strain relief loop according to various embodiments of a medical lead.

FIGS. 4A and 4B show an example of a lead 104' that has a modified lead body portion 402 present at the intersection point 110. In this example, the modified lead body portion 402 has a greater diameter and hence a greater thickness than the remainder of the medical lead 104'. This increased thickness at the modified portion 402 maintains a greater separation between internal conductive items of the medical lead 104' such as filar conductors and/or shields of the intersecting passes of the medical lead 104 at the intersection point 110. Such separation reduces the amount of RF heating that is produced by the intersection point 110. This separation is best viewed in the cross-sectional view of FIG. 4B take at the intersection point, where the shields 206 and conductors 202 of each pass of the lead 104 have increased separation due to the enlarged lead body portion 402.

Additionally, the increased thickness of the modified portion 402 creates a greater separation between the conductive items within the medical lead 104' at the intersection point 110 and the tissue of the patient present at the intersection point 110. Thus, the tissue of the patient is also better insulated from the RF heating by the modified portion 402. In FIG. 4B, the modified portion 402 is present on one pass of the lead 104. If the same amount of separate of the shield 206 and conductors 202 are desired for both passes, then both passes of the lead shown in FIG. 4B would be provided with the increased thickness as shown for modified portion 402.

Figure 5:
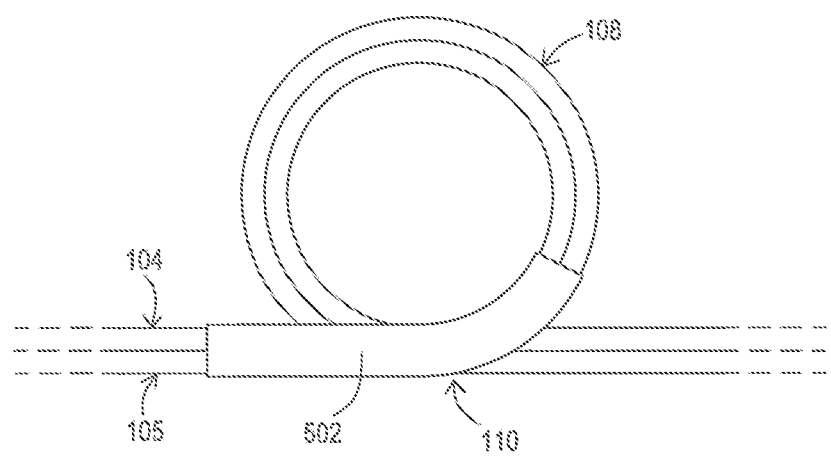
FIG. 5 shows another example of the forced strain relief loop according to various embodiments of a medical lead where a protective band is present about two adjacent leads.

FIG. 5 shows an example of two adjacent medical leads 104, 105 that also includes a sleeve 502 positioned on the medical leads 104, 105 so as to cover the medical leads 104, 105 at the intersection point 110 of both. This sleeve 502 may be installed on the leads 104, 105 prior to forming the strain relief loops 108 and the sleeve 502 can be formed into the loop configuration as well. Alternatively, the sleeve 502 can be added after the loops 108 have been formed. The sleeve 502 may be constructed of materials such as PEEK, polyurethane, silicone, and the like. The sleeve 502 provides the same benefits as the modified portion 402 of FIG. 4. The sleeve 502 provides separation of conductive items between the two passes of the lead body 104 at the intersection point 110 to reduce overall RF heating of the intersection point 110. Additionally, the sleeve 502 provides an additional layer of insulation to further separate the conductive items of the medical lead 104 at the intersection point 110 from the tissue of the patient. For embodiments where multiple leads 104, 104 are looped adjacently as shown, an alternative is for a sleeve 502 to be present on each lead 104, 105 individually rather than a single sleeve 502 surrounding the multiple lead bodies. Additionally, a sleeve 502 may be providing around the medical lead 104 for scenarios where only the single medical lead 104 is present.

While embodiments have been particularly shown and described, it will be understood by those skilled in the art that various other changes in the form and details may be made therein without departing from the spirit and scope of the invention.

What is claimed is:

1. A medical lead, comprising:
    an insulative lead body having a formed loop such that the insulative lead body imposes a force to regain the formed loop when the formed loop is disturbed wherein the formed loop creates an intersection point of the insulative lead body;
    at least one electrical conductor surrounded by the insulative lead body;
    at least one electrical contact on a proximal end of the lead body, the at least one electrical contact being electrically coupled to the at least one electrical conductor; and
    at least one electrode on a distal end of the lead body, the at least one electrode being electrically coupled to the at least one electrical conductor.

2. The medical lead of claim 1, wherein the insulative lead body has a greater thickness at the intersection point.

3. The medical lead of claim 1, further comprising a sleeve that is positioned over the insulative body at the intersection point.

4. The medical lead of claim 1, further comprising a conductive shield surrounding the conductor.

5. The medical lead of claim 4, wherein the insulative lead body surrounds the conductive shield.

6. The medical lead of claim 5, wherein the insulative lead body comprises an inner layer and an outer layer, wherein the inner layer surrounds the conductor, wherein the conductive shield surrounds the inner layer, and wherein the outer layer that surrounds the conductive shield.

7. A medical system, comprising:
    a medical device with a stimulation output connector; and
    a medical lead comprising:
    an insulative lead body having a formed loop such that the insulative lead body imposes a force to regain the formed loop when the formed loop is disturbed, wherein the formed loop creates an intersection point of the insulative lead body;
    at least one electrical conductor surrounded by the insulative lead body;
    at least one electrical contact on a proximal end of the lead body, the at least one electrical contact being electrically coupled to the at least one electrical conductor and in electrical contact with the stimulation output connector; and
    at least one electrode on a distal end of the lead body, the at least one electrode being electrically coupled to the at least one electrical conductor.

8. The medical system of claim 7, wherein the insulative lead body has a greater thickness at the intersection point.

9. The medical system of claim 7, further comprising a sleeve that is positioned over the insulative body at the intersection point.

10. The medical system of claim 7, further comprising a conductive shield surrounding the conductor.

11. The medical system of claim 10, wherein the insulative lead body surrounds the conductive shield.

12. The medical system of claim 11, wherein the insulative lead body comprises an inner layer and an outer layer, wherein the inner layer surrounds the conductor, wherein the conductive shield surrounds the inner layer, and wherein the outer layer that surrounds the conductive shield.

13. A method of making a medical lead, comprising:
surrounding a conductor with an insulative lead body;
mounting a contact on a proximal end of the insulative lead body and in electrical connection to the conductor;
mounting an electrode on a distal end of the insulative lead body and in electrical connection to the conductor; and
forming a loop in the insulative lead body such that the insulative lead body imposes a force to regain the formed loop when the formed loop is disturbed, wherein the formed loop creates an intersection point of the insulative lead body.

14. The method of claim 13, wherein forming the loop comprises placing the insulative body within a mold that holds the insulative body in the loop and heating the insulative body within the mold.

15. The method of claim 13, wherein surrounding the conductor with an insulative body comprises surrounding the conductor with an inner insulative lead body portion, the method further comprising surrounding the inner insulative lead body portion with a conductive shield, and wherein surrounding the conductor with the insulative body further comprises surrounding the conductive shield with an outer insulative body portion.

\* \* \* \* \*